United States Patent
Klever et al.

(10) Patent No.: US 12,089,886 B2
(45) Date of Patent: Sep. 17, 2024

(54) CRYOGENIC APPLICATOR

(71) Applicant: Dutch Renewable Energy B.V., Muiden (NL)

(72) Inventors: Diede Hendrik Paul Klever, Muiden (NL); Hubert Clemens Pellikaan, Utrecht (NL)

(73) Assignee: Dutch Renewable Energy B.V., Muiden (NL)

( * ) Notice: Subject to any disclaimer, the term of this patent is extended or adjusted under 35 U.S.C. 154(b) by 575 days.

(21) Appl. No.: 17/423,136

(22) PCT Filed: Jan. 15, 2020

(86) PCT No.: PCT/EP2020/050881
§ 371 (c)(1),
(2) Date: Jul. 15, 2021

(87) PCT Pub. No.: WO2020/148318
PCT Pub. Date: Jul. 23, 2020

(65) Prior Publication Data
US 2022/0133380 A1    May 5, 2022

(30) Foreign Application Priority Data
Jan. 18, 2019  (EP) .................................... 19152564

(51) Int. Cl.
*A61K 45/06*  (2006.01)
*A61B 18/02*  (2006.01)
*A61B 18/00*  (2006.01)

(52) U.S. Cl.
CPC .......... *A61B 18/0218* (2013.01); *A61K 45/06* (2013.01); *A61B 2018/00017* (2013.01);
(Continued)

(58) Field of Classification Search
CPC ................ A61B 18/0218; A61B 18/02; A61B 2018/00017; A61B 2018/00029;
(Continued)

(56) References Cited

U.S. PATENT DOCUMENTS

| | | | |
|---|---|---|---|
| 5,516,505 A * | 5/1996 | McDow ............. | A61B 18/0218 604/289 |
| 10,531,981 B2 | 1/2020 | Herweijer et al. | |
| 2017/0189627 A1 * | 7/2017 | Klever ................ | A61M 35/003 |

FOREIGN PATENT DOCUMENTS

| | | |
|---|---|---|
| WO | 2006/004407 A2 | 1/2006 |
| WO | 2016/010428 A1 | 1/2016 |
| WO | 2016/178161 A1 | 11/2016 |

OTHER PUBLICATIONS

"lees de gehele bijsluiter voordat u wartner gebruikt", Bijsluiter Wartner Wrattenverwijderaar, Jun. 30, 1999 (Jun. 30, 1999), page complete XP002107834, p. 2.

* cited by examiner

*Primary Examiner* — Ankit D Tejani
*Assistant Examiner* — Joshua Brendon Solomon
(74) *Attorney, Agent, or Firm* — N.V. Nederlandsch Octrooibureau

(57) ABSTRACT

An applicator for applying cryogenic fluid to a treatment area is described, the applicator comprising: a reservoir (12) configured to contain a cryogenic fluid comprising a gas phase (G) and a liquid phase (L). A nozzle (20) extends from a proximal end arranged in fluid communication with the reservoir (12) to an open distal end (21) for application of fluid to a treatment area. An actuatable valve is provided to selectively allow a flow of cryogenic fluid from the reservoir (12) through the distal end of the nozzle (20). A spacer (14) extends distally beyond the distal end (21) of the nozzle (20), the spacer (14) comprising a skin contacting surface
(Continued)

(14*a*) at its distal end. A porous material (16) is provided between the distal end (21) of the nozzle (20), at least between the open end of the nozzle and the skin contacting surface of the spacer.

17 Claims, 6 Drawing Sheets

(52) U.S. Cl.
CPC ............... *A61B 2018/00029* (2013.01); *A61B 2018/00065* (2013.01); *A61B 2018/0047* (2013.01)

(58) Field of Classification Search
CPC .. A61B 2018/00065; A61B 2018/0047; A61B 2018/00452; A61B 2090/036; A61K 45/06; A61F 2007/0052; A61F 2007/0063; A61F 2007/0087
See application file for complete search history.

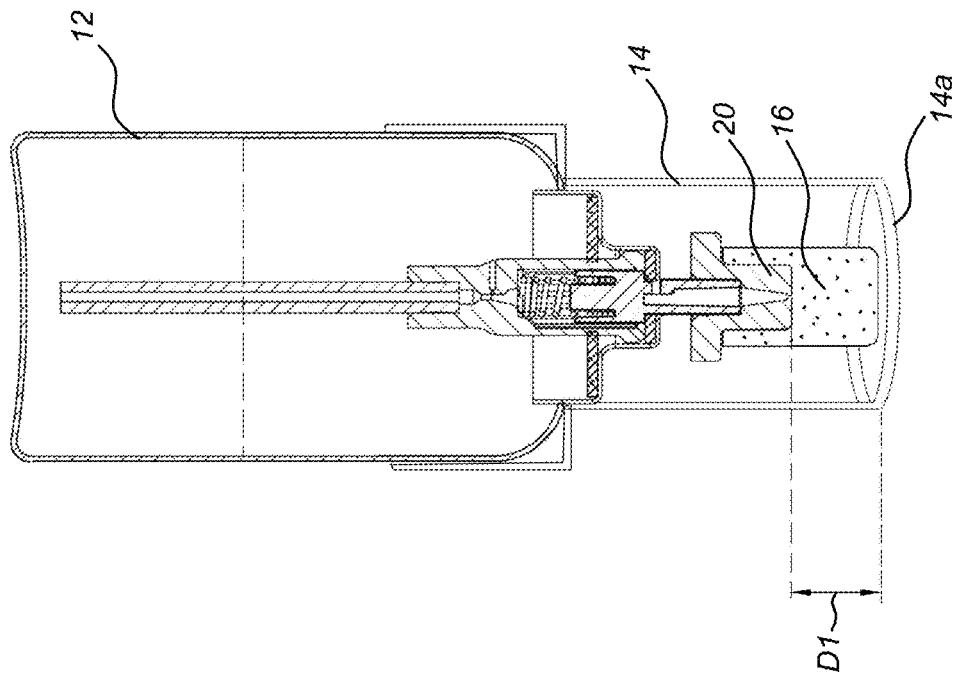
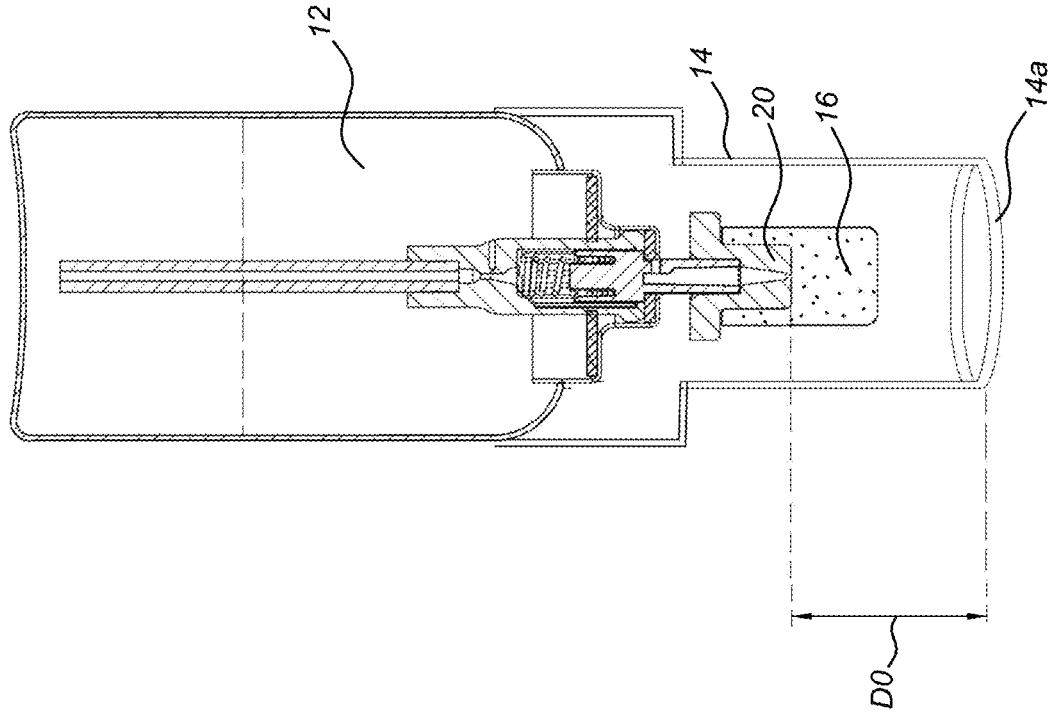

CRYOGENIC APPLICATOR

FIELD OF THE INVENTION

The present invention relates to an applicator for administering a quantity of liquid cooling agent, e.g. a cryogenic fluid, to an area of skin for treatment.

BACKGROUND OF THE INVENTION

Skin treatments to improve the appearance of skin are widely applied. Skin conditions often targeted by such treatments include warts, moles, freckles, skin tags, age spots (also known as liver spots), lentigines, or other skin-related abnormalities.

Known treatments for such skin conditions include the application of topical lotions containing acids, bleaching agents, vitamins and other active ingredients to treat the underlying condition or reduce the pigmentation in the affected skin. Such topically applied lotions are convenient and generally suitable for home use, however such treatments are generally slow, result in subtle improvement of the skin, or may cause hypo- or hyper-pigmentation.

The application of laser energy to the skin in the form of laser therapy is also known for the treatment of common skin conditions. However, laser therapy is generally not suitable for home use, is expensive, and can cause unnecessary pain and scarring in the treatment area.

Cryogenic treatments, in which a cryogenic agent (e.g. liquid nitrogen or another cryogen) is applied to the skin, are fast acting, effective and can be used at home. However, to ensure safe and effective use of cryogenic treatments, the application of cryogenic fluid to the skin should be carried out in a controlled manner. Cooling the treatment area to too low a temperature can cause excessive damage to the tissue. Cooling the treatment area for too long a duration can lead to excessive cooling of the surrounding healthy tissue, which increases the size of the affected area. Very prolonged exposure to excessively cold temperatures can lead to tissue necrosis. Therefore, the manner in which cryogenic fluid is applied, and the duration for which is it applied to the tissue should be carefully managed.

WO 99/49797 relates to a device for administering a quantity of cryogenic fluid to an area of skin for treatment of skin conditions. The device comprises a reservoir of cryogenic fluid and an opening closed by an actuatable valve through which cryogenic fluid can be dispensed from the reservoir. A treatment end of the device comprises a sponge, in fluid communication with the opening, which can be pressed against a treatment area.

WO 2016/178161 related to a pen for the treatment of dermatological disorders, such as warts, by means of a coolant. The pen comprises a distal part comprising a holder for the storage of a coolant and a proximal part comprising an applicator for the administration of the coolant to the dermatological surface to treat. The pen may further comprise an applicator for administering low temperatures to one or more warts to treat, wherein the applicator may have a porous structure.

SUMMARY OF THE INVENTION

In a first aspect of the invention, there is provided an applicator for applying cryogenic fluid to a treatment area, the applicator comprising: a reservoir configured to contain a cryogenic fluid comprising a gas phase and a liquid phase; a nozzle arranged in fluid communication with the reservoir to allow dispensing of cryogen from the reservoir through an open distal end of the nozzle to a treatment area; an actuatable valve configured to selectively allow a flow of cryogenic fluid from the reservoir through the open distal end of the nozzle; an actuator configured to selectively actuate the actuatable valve; a spacer extending distally beyond the distal end of the nozzle, the spacer comprising a skin contacting surface at its distal end; and a porous material extending (in a longitudinal direction) at least between the open end of the nozzle and the skin contacting surface of the spacer.

By providing a porous material between the open end of the nozzle and the skin contacting surface of the spacer, the cryogenic fluid can be dispensed into the porous material, which is configured to be brought into contact with the skin to be treated. This can ensure that the cryogenic fluid is efficiently and effectively delivered to the treatment site. As will become apparent from the following detailed description, embodiments of the present invention may also allow continuous application of cryogenic fluid to the treatment site, which can provide more effective treatment than a pre-loaded application sponge configured to be pressed against the treatment site.

The actuatable valve comprises: a mixing chamber, preferably having an operational internal volume of 10-600 µl, and comprising an inlet and an outlet, wherein the inlet comprises a Venturi tube having an entry cone for receiving gas phase from the container, the entry cone preferably being connected to a drawing tube that extends into the reservoir, an exit cone and a constricted section that connects the entry cone with the exit cone, said constricted section or said exit cone comprising a liquid inlet for receiving liquid phase from the container, the liquid inlet having a first cross-sectional opening area and the constricted section having a second cross-sectional opening area that is at least 150% larger than the first cross-sectional area, and wherein the nozzle is connected to the outlet of the mixing chamber.

The entry cone of the Venturi tube can be connected to a drawing tube that extends into the container. The liquid inlet of the Venturi tube can connect the constricted section or the exit cone of the Venturi tube with the interior of the container adjacent to the valve. The constricted section of the Venturi tube can have a cross-sectional opening area of 0.12 to 0.5 mm$^2$. The Venturi tube can have an entry cone of 30-90 degrees and an exit cone of 10-40 degrees.

The actuatable valve can optionally comprise a fixed part fixed to the container and comprising the Venturi tube and the liquid inlet and forming a circumferential sidewall of the mixing chamber, the valve further comprising a moveable part that is moveable with respect to the fixed part between a valve-open position and a valve-closed position, said moveable part comprising the nozzle, wherein the nozzle has a circumferential side wall surrounding a channel for the liquid-in-gas dispersion and a through opening in said side wall, wherein the through opening is arranged such that in the valve-open position the through opening fluidly connects the mixing chamber and the orifice of the nozzle, and in the valve-closed position the moveable part and fixed part together seal off a passage between the mixing chamber and the through opening.

The distal end of the nozzle may be spaced from the skin contacting surface of the spacer by a minimum distance D1, wherein D1 is preferably between 2 mm and 15 mm, and more preferably between 4 mm and 8 mm.

The distance between the between the skin contacting surface and the open end of the nozzle can be variable between the minimum distance D1 and an initial distance D0, wherein D0 is greater than D1.

Optionally, a delivery tube can be connected to the open end of the nozzle, and can provide a conduit through which fluid discharged from the nozzle is delivered to the porous material. The optional delivery tube (when present) is disposed with its open end proximal of the skin contacting surface of the spacer. In other words, the skin contacting surface of the spacer extends beyond the open distal end of the delivery tube such that the opening of the delivery tube is spaced from the skin when the device is held against the area of skin to be treated. Preferable, the open distal end of the delivery tube is spaced apart from the skin contacting surface (in the longitudinal direction) by at least 1 mm, more preferably at least 2 mm, and more preferably at least 4 mm.

In some examples, the spacer can be moveable with respect to the nozzle and/or the reservoir from a first position to a second position.

For example, the spacer can be movably mounted with respect to the nozzle to allow the porous material to be brought into contact with the skin by pressing the spacer against the skin and moving the spacer with respect to the nozzle in a proximal direction. This feature can also be combined with a tapered sponge to provide a variable contact area for the porous material against the skin, wherein the further the spacer is moved proximally with respect to the nozzle, the greater the area of porous material is brought into contact with the skin.

Movement of the spacer can be configured to actuate the actuatable valve to deliver cryogenic fluid to the treatment site. For example, movement of the spacer in a proximal direction with respect to the housing can be used to open the actuatable valve. The device can therefore be configured to actuate the actuatable valve by pressing the spacer against the skin.

Actuator-spacers can be configured for relative movement with respect to the nozzle and the reservoir, or for relative movement with respect to the housing, whilst remaining fixed with respect to the nozzle. For example, the spacer may be fixedly mounted with respect to the nozzle such that movement of the spacer relative to the reservoir towards a dispensing position also results in movement of the nozzle. The spacer and the nozzle thus move together to actuate the actuatable valve.

Where the spacer and/or the nozzle moves with respect to the housing to actuate the actuatable valve, the distance D1 is defined with the spacer in the position in which the actuatable valve is open. In other words, the device is configured such that the minimum distance D1 is maintained during delivery of the cryogenic fluid.

The spacer can take different forms and may comprise a deformable spacer, e.g. a spring, a moveable projection, e.g. a slidable spacing projection; and/or a fixed projection. The deformable spacer can be mounted to the reservoir or the nozzle.

The skin contacting surface can be configured to define a perimeter around the area to be treated. That is, the skin contacting surface can comprise a hoop or ring (or a non-circular shape) having an opening in which the area to be treated can be placed. The opening defined within the perimeter is preferably aligned (in the logitudinal direction with the porous material, which is aligned (in the logitudinal direction) with the opening of the nozzle.

The skin contacting surface preferably defines a plane P. A distal surface of the porous material can extend in the plane P (and not project distally beyond the plane P); or a distal end of the porous material projects distally beyond plane P when the applicator is not in use.

In at least some embodiments, the applicator can further comprise at least one flange, extending in a transverse direction with respect to the longitudinal axis of the applicator. The flange can be affixed to the nozzle or the reservoir and can provide a bearing surface against which the user can brace their finger(s) to actuate the device. The at least one flange can comprise a first flange and second flange, said first flange extending in substantially opposing directions, although other configurations are also possible.

The porous material can comprise any porous material that allows the cryogenic fluid to reach the treatment site. For example, the porous material can comprise a foam or sponge having an open cell structure between the opening of the nozzle and the distal end of the material.

In some embodiments, the sponge can comprise a region of open-cell foam at its distal end, and a region of closed-cell foam at its proximal end. The open-cell foam can be provided between the opening of the nozzle and the skin contacting surface to provide a flow path through which cryogenic fluid can travel. However, at least a portion of the sponge or porous material can be formed of a closed-cell foam, thereby limiting the flow of cryogenic fluid through that part of the sponge. For example, a closed-cell foam can be provided in the portion of the sponge proximal to the nozzle opening to prevent cryogenic fluid travelled away from the treatment site.

Generally, the sponge comprises a longitudinal cross-sectional profile that varies in width along its length, preferably from a narrower distal end to a wider proximal end. The variable width of the cross-section provides a variable contact surface area, wherein the user can vary the contact area by varying the compression of the porous material. For example, the profile can be selected from a tapered profile; a spherical profile; or an elliptical profile.

Additionally or alternatively, the sponge can comprise at its distal end a circumferential wall portion, and a recessed central portion, wherein the projection portion extends at least partially around a perimeter of the recessed portion.

Optionally, the porous material and/or the spacer can comprise a thermo-chromic composition, e.g. cyanidin chloride with dodecyl gallate and hexadecanoic acid.

The reservoir can contain a cryogenic fluid, the cryogenic fluid optionally comprising a pharmacologically active agent, or a chemically active agent, such as one or more of the following: an anaesthetic agent; an antibacterial agent; an antiviral agent; an anti-inflammatory agent; or a keratolytic agent.

In a second aspect of the invention, there is provided a kit comprising the applicator according to any of the embodiment described above, wherein the porous material is removably mounted on the nozzle, and the kit comprises additional porous components having different shapes and/or sizes.

BRIEF DESCRIPTION OF THE DRAWINGS

The invention will now be described in more detail with reference to a number of non-limiting, illustrative examples, which:

FIGS. 3A and 3B show a cryogenic applicator according to the invention during operation;

DETAILED DESCRIPTION OF THE DRAWINGS

Figure 1:
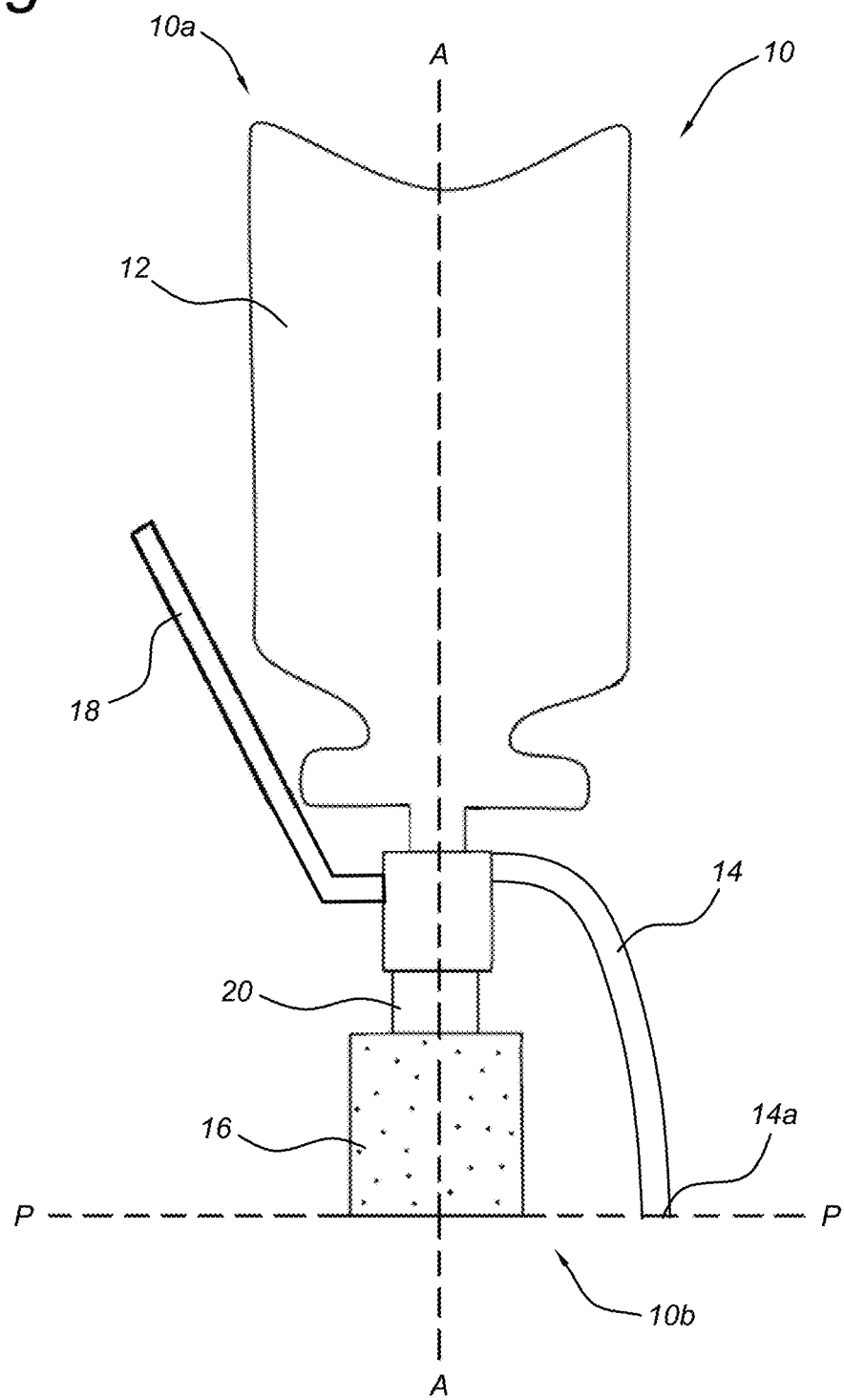
FIG. 1 shows a cryogenic applicator according to an embodiment of the invention.

FIG. 1 shows a cryogenic applicator according to an embodiment of the invention. The applicator 10 extends from a proximal end 10a to a distal end 10b and comprises a reservoir 12, a spacer 14, a porous material 16, and an actuator 18. Optionally, the reservoir can be disposed within a housing (not shown).

The reservoir 12 is configured to store a volume of cryogenic fluid (e.g. dimethyl ether or another fluid) and comprises an outlet at its distal end through which fluid can be selectively dispensed. The outlet is closed by an actuatable valve (not shown in FIG. 1), which is configured to be selectively opened to allow cryogenic fluid to be dispensed for application to a treatment area through the nozzle 20.

The spacer 14 extends from the distal end of the reservoir 12 and comprises a skin contacting surface 14a at its distalmost end, which is configured to be placed against a skin surface area during a treatment procedure. The spacer 14, with its skin contacting surface 14a, helps to maintain a predetermined minimum distance between the outlet of the nozzle 20 and the area of skin to be treated.

In the embodiment shown in FIG. 1, the spacer 14 comprises an arm or claw that extends distally from the reservoir 12. The spacer 14 terminates at the skin contacting surface 14a in a plane P, which is perpendicular to the longitudinal axis A of the applicator 10. When the skin contacting surface 14a of the spacer 14 is brought into contact with the area of skin to be treated, the plane P is brought into contact with and approximates the surface of the skin.

Although the embodiment shown in FIG. 1 shows a spacer 14 comprising a single arm or claw, the skilled person will appreciate that additional arms or claws may be provided. For example, two diametrically opposed arms may be provided, one either side of the nozzle. Embodiments with three or more arms are also possible. The spacer can also comprise a hoop or ring disposed at the end of one of more arms extending from the reservoir or housing. The distally facing surface of the ring or hoop provides the skin contacting surface 14a. The spacer can also comprise a moveable or deformable component. Such embodiments allow the user to place the applicator against the skin to be treated, and to vary the minimum distance between the skin and the outlet of the nozzle by varying the pressure applied to the applicator. Such embodiments will be described in more detail below.

In at least some embodiments, the skin contacting surface 14a is flat or planar, and extends in the plane P perpendicular to the longitudinal axis A of the device. However, the skilled person will appreciate that the skin contacting surface 14a can have a non-planar surface. In this case, the distal most part of the skin contacting surface 14a lies in the plane P that approximates the skin surface.

A porous material, e.g. sponge 16, is positioned distal of the reservoir 12 and covers the open end of a nozzle (not shown in FIG. 1). The nozzle will be described in more detail with reference to FIGS. 2 to 6.

As shown in FIG. 1, the sponge 16 extends distally from the reservoir 12 and terminates in plane P. The sponge 16 serves to provide a porous matrix that can be filled with cryogenic fluid from the reservoir 12 and brought into contact with the area of skin to be treated. Since the sponge 16 is porous and compressible, it can also be configured to extend beyond plane P.

An actuator is configured to actuate controlled release of cryogenic fluid from the reservoir 12. In the embodiment shown in FIG. 1, the actuator 1 takes the form of a lever 18, configured to open the selectively actuatable valve. However, the skilled person will understand that other actuation means can be employed. For example, an actuator can be provided in which the user pushes the reservoir forward with respect to the spacer to actuate the valve. Alternative actuation assemblies will be discussed in further detail below.

Figure 2:
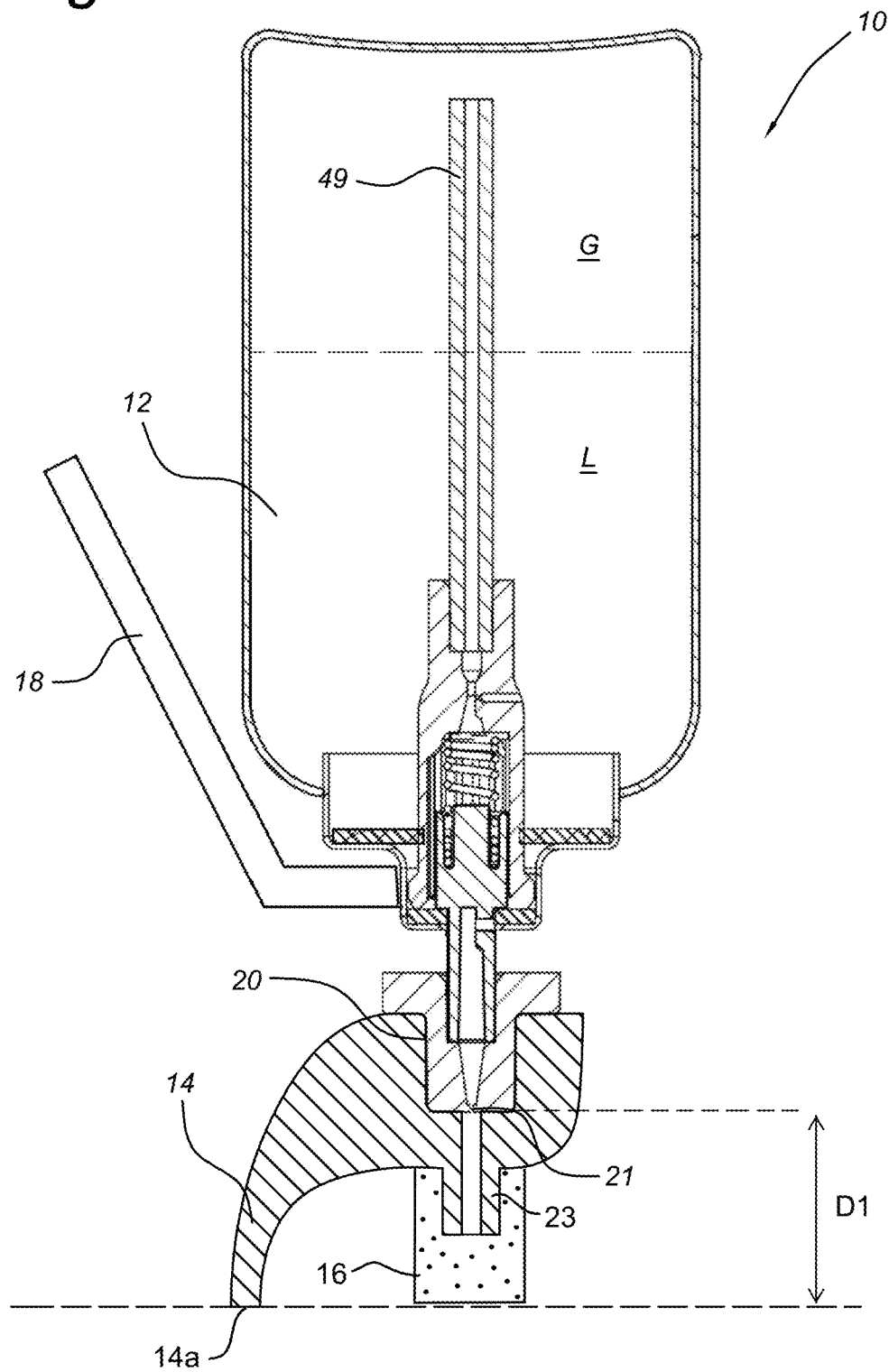
FIG. 2 shows a cross-sectional view of the device of FIG. 1.

FIG. 2 shows a cross-sectional view of the applicator 10 of FIG. 1. As shown in FIG. 2, the reservoir 12 is in fluid communication with a nozzle 20. The nozzle 20 extends from a proximal end in fluid communication with the reservoir 12 to an open distal end 21, from which fluid contained in the reservoir 12 can be dispensed. The open end 21 of the nozzle 20 is spaced apart from the skin contacting surface 14a of the spacer 14 by a distance D. In other words, the distal end of the spacer extends beyond the open end of the nozzle 20, such that the distal end of the nozzle 20 is positioned between the reservoir 12 and the skin contacting surface 14a. This ensures that the spacer prevents or resists the open end of the nozzle 20 being brought into direct contact with the surface of the skin. Although the nozzle 20 is shown in FIG. 1 as comprising two interconnected parts, the skilled person will appreciate that the nozzle 20 can also comprise a single component, or three or more parts. The nozzle 20 is configured to deliver cryogenic fluid from the reservoir 12 to the treatment site, and thus comprises a channel through which cryogenic fluid can flow from the interior of the reservoir 12 to the open end 21 of the nozzle.

The embodiment shown in FIG. 2 further comprises an optional delivery tube 23, which is fluidically coupled to the open end 21 of the nozzle 20 and is configured to provide a conduit through which fluid discharged from the nozzle is delivered to the porous material 16. As shown in FIG. 2, the open distal end of the delivery tube 23 is located proximal of the skin contacting surface 14a of the spacer 14. This is to ensure that the delivery tube 23 delivers cryogenic fluid to the porous material 16, which in turn brings the cryogenic material into contact with the treatment site. In other words, in embodiments in which a delivery tube 23 is provided, the skin contacting surface 14a extends beyond the distal end of the delivery tube to ensure that there is a volume of porous material 16 into which the cryogenic fluid can be dispensed The delivery tube 23 shown in FIG. 2 is an optional feature of the invention as is not required in order for the cryogenic fluid to be dispensed into the porous material 16. Instead, and as shown in FIGS. 4A-4D, the open end 21 of the nozzle 20 can open directly into the porous material 16. However the delivery tube 23 can provide additional advantages in some aspects of the present invention by delivering the cryogenic fluid to the distal end of the porous material 16. It can also provide a convenient projection on which to mount the porous material, which may also be integrated into a component that also provides the spacer.

In embodiments of the invention that do comprise a deliver tube 23, the open distal end of the delivery tube 23 is preferably spaced (in the longitudinal direction) from the skin contacting surface by a distance of at least 1 mm, more preferably at least 2 mm, and more preferably at least 4 mm.

Moreover, to provide an unimpeded flow path between the open end 21 of the nozzle 21 and the porous material 16, the inner bore of the delivery tube preferably has an inner diameter that is larger than the inner diameter of the open end of the nozzle 21. The internal bore of the delivery tube 23 preferably comprises a cross-sectional area that is at least twice as large as the cross-sectional area of the open end of the nozzle 21, more preferably at least 4 times larger, and more preferably at least 10 times larger.

The spacer 14 maintains a minimum distance D1 between the distal end 21 of the nozzle 20 and the skin contacting surface 14a. In embodiments in which the position of the spacer 14 is fixed with respect to the nozzle 20, the D=D1 at all times. However, as will become apparent from the following description, in some embodiments, the spacer can be configured to be movable with respect to the nozzle 20. In such embodiments, the distance D1 is the minimum distance between the skin contacting surface 14a of the spacer 14 and the open end 21 of the nozzle 20. In preferred embodiments (and all configurations illustrated herein), distance D1 is in the range of: 2-15 mm, more preferably 4-8 mm.

As mentioned above, a selectively actuatable valve prevents fluid communication between the reservoir 12 and the opening of the nozzle 20 until actuator 18 is actuated. The valve and actuator combination can take any form known in the art. For example, the valve can comprise a ball valve. With the actuator 18 in a first position, a ball (or other closure member) seals against a valve seat, thereby preventing egress of cryogenic fluid from the reservoir 12. Upon actuation of the actuator 18 to a second position, the ball (or other closure member) is moved against its bias away from the valve seat to allow cryogenic fluid to flow from the reservoir 12 towards the outlet of the nozzle 20, and into the sponge 16.

A preferred embodiment of the invention, in which a valve assembly comprises a Venturi tube will be described in more detail with reference to FIG. 6.

Referring now to FIGS. 3A and 3B, in at least some embodiments, the actuator and the spacer can be combined, such that relative movement between the spacer 14 and the reservoir actuates the valve to dispense cryogenic fluid through the nozzle 20. Relative movement of the spacer 14 with respect to the reservoir 12 can be as a result of, for example, the user pressing the skin contacting surface 14a against the surface of the skin. Although the coupling between the spacer 14 and the valve is not shown in FIGS. 3A and 3B, in the embodiment of FIGS. 3A and 3B, movement of the spacer 14 from the first position (FIG. 3A) to the second position (FIG. 3B) is configured to actuate the actuatable valve.

In an alternative embodiment similar to the embodiment shown in FIGS. 3A and 3B, the spacer 14 can be configured for relative movement with respect to the reservoir 12 and the nozzle 20 can be configured for relative movement with respect to the reservoir 12. In such embodiments, movement of the nozzle with respect to the reservoir can be configured to actuate the actuatable valve.

As shown in FIG. 3A, and similarly to FIG. 2, an embodiment of the present invention comprises a reservoir 12, a dispensing nozzle 20 and a porous material 16 disposed over at least a distal end 21 of the nozzle 20. In contrast to the embodiments described with reference to FIGS. 1 and 2, the embodiment shown in FIG. 3, the spacer 14 comprises a pair of arms supporting a ring or hoop that forms the skin contacting surface 14a. The spacer 14 is moveable with respect to the reservoir 12 between a first position (shown in FIG. 3A) and a second position (shown in FIG. 3B).

In the position shown in FIG. 3A, the distal end 20a of the nozzle 20 is spaced from the plane P of the skin contacting surface 14a by a distance D0. In this position, the sponge 16 is also located proximal of the skin contacting surface 14a. In this position, the valve closing the reservoir is sealed and cryogenic fluid is not dispensed from the nozzle opening.

Referring now to FIG. 3b, as the user presses the skin contacting surface 14a against the skin, the spacer 14 moves proximally with respect to the reservoir 12. In the illustrated embodiment, movement of the spacer 14 with respect to the reservoir 12 performs two functions: (i) actuation of the actuatable valve to allow fluid communication between the reservoir 12 and the outlet of the nozzle 20; and (ii) advancement of the sponge 16 with respect to the skin contacting surface 14a to bring the sponge 16 into contact with the skin.

The spacer 14 and or the porous material 16 can comprise or be treated with a thermo-chromic paint, which is configured to change temperature one a predetermined temperature range is reached. This feature can indicate cryogenic action to the user. As an alternative to a thermo-chromic paint, the sponge 16 and/or the spacer 14 can comprise a thermo-chromic dye, for example an organic leuco-dye. A suitable thermo-chromic system for use in connection with the present invention may be cyanidin chloride with dodecyl gallate and hexadecanoic acid.

The skilled person will appreciate that different actuation mechanisms may be incorporated into the dispenser, whilst still realising the advantages of the present invention.

Turning now to FIGS. 4A-4D, the sponge 16 and the actuation mechanism can take different forms. Each of the embodiments in FIGS. 4A-4D shows the distal end of a device according to the invention comprising a sponge 16, a nozzle 20, and a spacer 14. It will be appreciated that the actuation mechanisms and the sponges described with reference to these figures can be independently combined to provide embodiments of the invention now shown in the Figures.

Figure 4A:
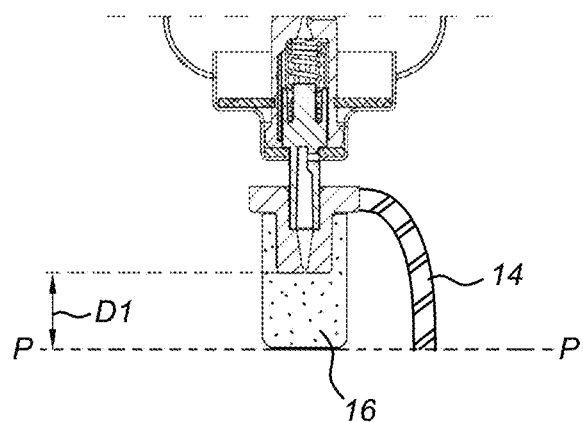
FIGS. 4A-4D show plan views of a treatment end of the device according to various embodiments.

In the embodiment shown in FIG. 4A, the sponge 16 comprises an open-cell foam that surrounds the distal opening 21 of nozzle 20, and surrounds the nozzle 20 along part of its length. In alternative, embodiment (not shown) the sponge 16 can surround the nozzle 20 along its entire length from its connection to the reservoir to its distal end 21.

The nozzle 20 comprises an optional flange that prevents the sponge 16 from being pushed further onto the nozzle 20. This can ensure that the sponge 16 maintains in position relative to the spacer, even when the sponge 16 is brought into contact with the skin.

The spacer 14 extends from the nozzle 20 and is fixedly connected thereto. The fixed connection between the nozzle 20 and the spacer 14 means that the distance between the open end 21 of the nozzle 20 and the skin contacting surface 14a of the spacer remains fixed at the minimum distance D1.

The actuatable valve is actuated by pressing the spacer 14 against the skin adjacent to the treatment site, with the sponge 16 positioned over the area to be treated. As the user presses the applicator against the skin, the nozzle 20 is pushed inwardly with respect to the housing to actuate the actuatable valve and deliver cryogenic fluid to the sponge 16. The spacer 14 maintains the minimum distance between the nozzle 20 and the skin surface, whilst the porous material acts as a conduit to bring the cryogenic fluid into contact with the treatment site in a controlled manner.

As shown in FIG. 4A, the sponge 16 forms a sheath around the nozzle, and extends beyond the open proximal end 21. The sponge extends at least a minimum distance D1. The minimum distance D1 is the minimum distance between the open end 21 of the nozzle 20 and the skin contacting surface 14a.

It will be appreciated that in the embodiment shown in FIG. 4A, the spacer is fixed with respect to the nozzle, and so the distance between the open end 21 of the nozzle 20 is fixed. However, in embodiments in which the spacer 14 is moveable with respect to the nozzle 20, the minimum distance D1 is defined between the open end of the nozzle 21 and the skin contacting surface 14a of the spacer 14, when the spacer 14 is in its fully retracted position with respect to the nozzle 21.

As shown in FIG. 4A, the skin contacting surface 14a of the spacer 14 and proximal end of the sponge 16 extend in the plane P. That is, the sponge 16 does not extend distally beyond the spacer 14. This means that when the spacer 14 is brought into contact with the surface of the skin, the sponge 16 is brought into contact with the area to be treated, with the sponge 16 substantially uncompressed. In the embodiment illustrated in FIG. 4A, the sponge 16 has a generally flat or planar distal surface. The cross-section of the sponge 16 at the proximal end is preferably circular. However, other cross-sectional shapes can be provided.

A distance D1 is defined between the open distal end of the nozzle 20 and the plane P in which the spacer 14 and the sponge 16 terminate. By providing a minimum distance D1 between the distal end of the nozzle 20 and the area to be treated (the distance being maintained at a minimum distance by the spacer 14), the porous material of the sponge 16 can be supplied with cryogenic fluid, which is brought into contact with the skin to be treated in a controlled manner (e.g. in a continuous manner, as will be described in more detail below).

Figure 4B:
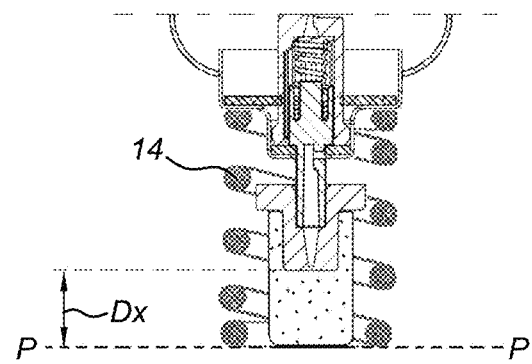

An alternative configuration is shown in FIG. 4B. As shown in FIG. 4B, the spacer 14 can comprise a deformable element, such as a helical spring. The helical spring 14 is arranged around the nozzle 20 and the sponge 16 such that its distal end provides a circumferential skin contacting surface. Because the spring is compressible, the distance D between the open end 21 of the nozzle 20 and the skin contacting surface 14a of the spacer 14 can be varied. In FIG. 4b, a variable distance Dx is therefore shown.

In its relaxed state, the spring 14 preferably extends slightly beyond the distal end of the sponge 16. The user can thus press the spring against the skin to bring the sponge 16 into contact with the area to be treated. The minimum distance D1 can defined as the point at which the depression of the spring will actuate the actuatable valve. Alternatively, the distance D1 can be the point at which the spring cannot be compressed any further (i.e. adjacent windings of the spring are brought into abutment) or the point at which the spring cannot be compressed further without exceeding a predetermined force. The predetermined force can be chosen depending on contact area of the spring to be brought into contact with the skin. The predetermined force can be, e.g. between 0.1 and 1N, e.g. 0.5N.

Figure 4C:
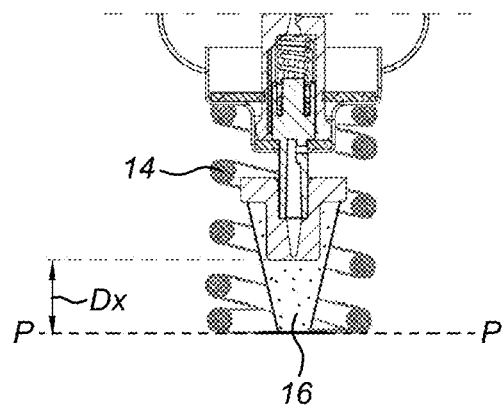

Yet another embodiment is show in FIG. 4C. As shown in FIG. 4C, the spacer 14 comprises a deformable element, such as a spring. However, in the embodiment shown in FIG. 4C, the sponge 16 tapers from a widest proximal portion toward a narrower distal portion. In the embodiment shown in FIG. 4C, the sponge 16 is generally conical in shape, however, other tapered shapes can be provided. Because the diameter of the sponge 16 varies along the longitudinal axis A, the combination of a tapered sponge in combination with the deformable spacer allows the user to vary the contact area of the sponge 16 with the area to be treated. As the user depresses the deformable spacer, the sponge 16 is compressed against the treatment site. Due to the taper of the sponge, the further the sponge is depressed, the larger the area of the sponge that is brought into contact with the target area. This can allow the user to modify the area of contact in accordance with the area to be treated.

The skilled person will appreciate that a deformable spacer is not required to achieve the above described advantages. Rather, the above described advantages can be achieved by combining a tapered sponge with a moveable spacer (as described with reference to FIGS. 3A and 3B) that provides a variable distance Dx between the nozzle 20 and the skin contacting surface 14a. In yet further embodiments, a static spacer can be combined with a tapered sponge 16 that extends beyond the skin contacting surface 14a of the spacer 14. In the latter embodiment, a minimum distance D1 is maintained between the nozzle 20 and the skin surface by the spacer 14, since the foam cannot be depressed beyond this point by bringing the device into abutting contact with the skin. However, the user will be able to vary the diameter of the sponge that is in contact with the treatment area by pressing the sponge against the skin until the minimum distance D1 is reached.

Figure 4D:
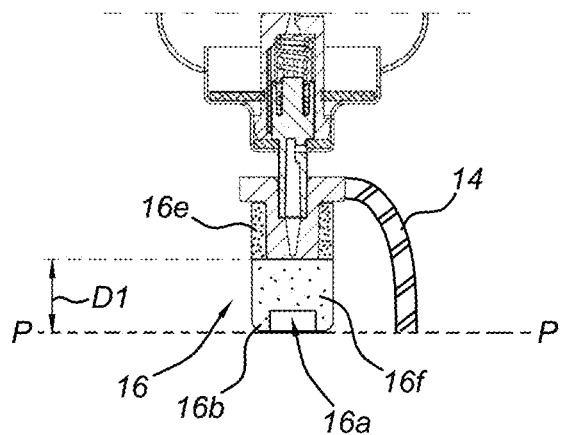

Yet another embodiment is shown in FIG. 4D. As shown in FIG. 4D, the sponge 16 can comprise a non-planar distal surface. For example, the sponge 16 can comprise a substantially cylindrical shape (as shown in FIG. 4A), except that at the distal end, the sponge 16 can comprises a proximally recessed central portion 16a and a distally projecting wall portion 16b that extends around a perimeter of the sponge 16. The wall portion surrounds the recess portion (wholly or partially) and provides a small localised void adjacent the treatment site into which cryogen can be dispensed from the open-cell foam of the sponge. It will be understood that the recessed portion can be combined with any of the above described embodiments. The combination of open- and closed-cell foam portions can be employed in any of the embodiments described herein.

In some embodiments, the peripheral wall portion 16b can extend only partially around the circumference of the void. This can advantageously allow a viewing opening so that the user can see the area to be treated.

The spacers and sponges described above are not limited to the combinations depicted in FIGS. 4A to 4D and it will be appreciated that the sprung spacer of FIGS. 4B and 4C can be combined with the sponge configurations of FIGS. 4A and 4D. Similarly, the sponges shown in FIGS. 4C and 4D can be combined with the assemblies of FIGS. 4A and 4B, and any of the nozzle, spacer, and actuation mechanisms described with reference to FIGS. 1 to 3. The present invention may also be provided as a kit, in which the applicator is provided with a plurality of different (detachable) sponges, each having a different shape, or diameter. Such a kit with removable and replaceable sponge portions can provide a range of contact surfaces to provide more tailored treatment to the user.

An optional but advantageous feature, applicable to all described embodiment of the invention, will now be described with reference to FIG. 4D. As shown in FIG. 4D, the sponge 16 can comprise a proximal portion 16e located proximal of the open end 21 of the nozzle 20 and a distal portion 16f, located distal of the open end 21 of the nozzle 20. The distal portion 16f comprises an open cell foam, as described above, which allows the cryogen dispensed from the open end 21 of the nozzle 20 to travel through the sponge 16, towards the treatment site. However, the proximal portion 16e of the sponge 16 comprises a closed cell-foam. The closed cell-foam does not allow the cryogen dispensed from the open end 21 of the nozzle 20 to travel through the sponge in the proximal direction, and thus the flow of cryogen is focused in the proximal direction, towards the treatment site.

In another embodiment (not illustrated), the open cell foam may be provided as a channel through the sponge 16 between the open end 21 of the nozzle 20 and the distal surface of the sponge 16. In such embodiments, and outer circumference of the sponge 16 is formed of a closed-cell foam whilst an inner core of open-cell foam provides a channel for cryogenic fluid flowing towards the treatment site. Such embodiments additionally prevent cryogenic fluid from exiting the porous material via the sides.

Figure 5:
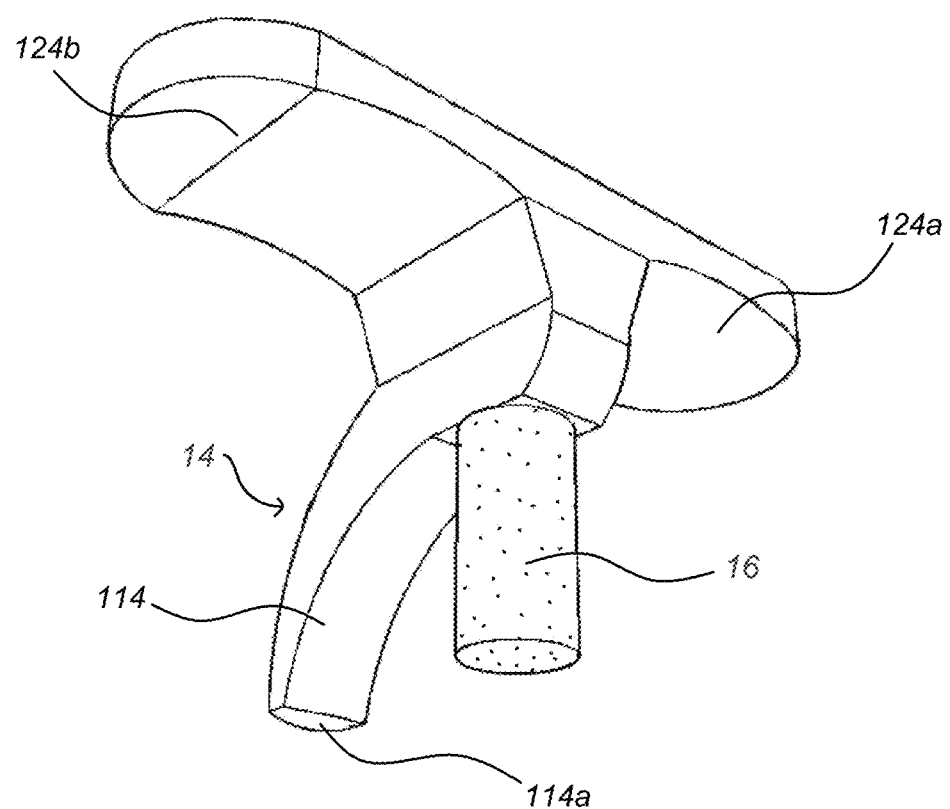
FIG. 5 shows a perspective view of an exemplary spacer according to a further embodiment.

Referring now to FIG. 5, the spacer 14 can be configured to maintain a minimum distance D1 between the distal end of the nozzle 20 and the treatment area at the same time as providing a grip and actuation surface for actuating the dispensing valve for the cryogenic fluid. For example, the device, and advantageously the spacer 14, can further comprise one or more flanges, configured to provide a distal bearing surface that extends substantially perpendicular to the longitudinal axis A of the applicator. The distal surface of the flange can provide a bearing surface against which the user can press to move the reservoir relative to the spacer (e.g. for actuation).

In the preferred embodiment shown in FIG. 5, the grip comprises a first flange 124a extending in a first direction on one side of the projection 114 and a second flange 124b extending in a second direction from a second side of the projection 114. The first and second directions above are generally perpendicular to the longitudinal axis A of the dispenser. The first and second flanges 124a, 124b shown above extend in opposite directions (with an angle of approximately 180 degrees defined between the flanges), although the skilled person will appreciate that the flanges 124a and 124b can also meet at a reflex angle (e.g. between 180 degrees and 360 degrees).

Although the first and second flanges 124a, 124b shown in FIG. 5 provide the dispenser with an intuitive syringe-like finger grip, the flange(s) may be provided in alternative configurations. For example, the flange may comprise a circumferential flange that extends perpendicular to the longitudinal axis, wholly or partially around the circumference of the proximal end of the reservoir 12 (or housing).

The flange(s) may provide a distally facing surface against which the user can brace the first and second fingers of one hand, at the same time as using the thumb of the same hand to actuate the valve, e.g. by pressing the reservoir 12 in a distal direction or by pressing an actuation button. By providing the spacing projection 114 and the grip together at the proximal end of the reservoir, the user can grip, position and actuate the device in a convenient manner with one hand, whilst maintaining good control of the position of the cryogen flow. The bearing surface provided by the grip also ensures that the user can exert the force necessary to actuate the valve, independently of the pressure applied to the target treatment side.

As shown in the exemplary embodiment in FIG. 5, the spacer/grip combination can comprise a spacer in the form of a claw or a distal projection 114, extending generally in the distal direction, to provide a skin contacting surface 114a at its distal end. The projection 114 may extend in an arc shape, from an initial lateral extension (away from the longitudinal axis at its proximal portion) and toward a longitudinal extension at the distal end.

The flange provides a distally facing surface against which the user can brace the first and second fingers of one hand, at the same time as using the thumb of the same hand to actuate the valve, e.g. by pressing the reservoir in a distal direction or by pressing an actuation button. By providing the spacing projection 114 and the grip together at the proximal end of the reservoir, the user can grip, position and actuate the device in a convenient manner with one hand, whilst maintaining good control of the position of the cryogen flow.

The spacer and grip combination of FIG. 5 is the spacer shown as a cross-sectional view in FIG. 2. However, the cross-section shown in FIG. 2 does not show the flanges 124a and 124b since these are oriented extending directly into and out of the page, as illustrated in the 2D cross-sectional representation of FIG. 2.

Advantageously, the grip and spacer combination of FIG. 5 can be conveniently mounted over the nozzle 20 shown in FIG. 2. To ensure that the mounted spacer shown in FIG. 5 and FIG. 2 does not slide proximally with respect to the nozzle 20 as the device is pressed against the skin, the nozzle comprises at least one abutment projection that extends radially from the nozzle body.

A preferred actuation assembly and mode of cryogen dispensing will now be described with reference to FIG. 6 in combination with FIG. 2. As shown in FIG. 6, a valve assembly comprises a valve 30 moveable between: (i) a closed position in which fluid communication between the interior of the reservoir 12 and the open end 21 of the nozzle 20 is prevented; and (ii) an open position, in which fluid communication between the interior of the reservoir 12 and the open end 21 of the nozzle 20 is permitted.

The reservoir 12 has an interval volume of approximately 10-200 ml and is configured to contain a liquid phase L and a gas phase G, which are in direct contact with each other (see FIG. 2). In the embodiment shown in FIG. 2, the liquid phase L is shown in the lower part of the reservoir 12, and the gas phase G is shown in the upper part of the reservoir 12. In an exemplary embodiment, the liquid phase L and the gas phase G are at a pressure of approximately 4 bar, and the liquid phase L comprises or consists of a liquefied dimethyl ether. Alternatively, the liquid phase 11 may consist of a 3:1. (w/w) mixture liquefied dimethyl ether and liquefied propane.

The nozzle 20 can be attached to the reservoir 12 and comprises an orifice at the distal end 21. The orifice 21 of the nozzle 20 has a relatively small cross-sectional opening area in the range of 0.018-0.07 $mm^2$ through which a directed spray of liquid-in-gas dispersion can be ejected into the sponge 16.

The valve 30 comprises a fixed part 38 that is fixed to the reservoir 12, and a moveable part 39 which is moveable relative to the reservoir 12 between a valve-closed position. FIG. 6 shows the valve assembly 30 in the valve-open position. The moveable part 39 and the fixed part 38 together form a mixing chamber 31 with an inlet 32 for supply of liquid phase and gas phase G to the mixing chamber 31.

The volume of the mixing chamber 31 depends on the position of the moveable part 39 relative to the fixed part, and has a volume of about 200 μl when the upon full actuation of the valve to the valve-open position.

For receiving gas phase G from the container, the inlet 32 is provided with a Venturi tube 44 having an entry cone 45 that in turn is connected to a drawing tube 49 that extends into the reservoir and comprises an open proximal end. The open proximal end of the drawing tube 49 is preferably provided in a proximal part of the reservoir 12 (i.e. away from the valve end of the reservoir 12). The open end of the drawing tube 49 is preferably located in a proximal 50% of the reservoir 12, more preferably a proximal 30%, more preferably a proximal 20%, as measured in the longitudinal direction.

The liquid inlet tube 48 is preferably provided in the distal part of the reservoir 12. That is, the liquid inlet 48 is preferably provided in a distal 50% of the reservoir 12, more preferably a distal 30%, more preferably a distal 20% and more preferably a distal 15% of the reservoir 12.

In exemplary embodiments, it is preferred that during the complete use cycle of the dispensing system, the open end of the drawing tube 49 does not extend into the gas phase G within the container when the dispensing system is in a top-up position (FIG. 2 shows a top-down position). Thus, no cryogenic dispersion is released from the dispensing system when the valve is actuated in the top-up position.

However, when the valve is actuated in the top-down position, the gas phase G enters the mixing chamber through the Venturi tube 44 and the resulting Venturi effect can draw up the liquid phase L through the liquid inlet 48 into the Venturi tube if there still is sufficient liquid phase L present in the container to feed into the liquid inlet. The Venturi effect also causes dispersal of the liquid phase L into the gas phase G under the formation of the cryogenic dispersion.

The Venturi tube 44 tapers towards a constricted section 46 to which it is connected, the section 46 being in turn is connected to an exit cone 47 that opens into the mixing chamber 31. The constricted section 46 further comprises a liquid inlet 48 for receiving liquid phase L from the reservoir 12. When the device is in the top-down position and the moveable part 29 is moved in the valve-open position, as shown in FIG. 6, and the propellant gas flows through the Venturi tube 44, causing under-pressure in the liquid inlet 48, as a result of which liquid is drawn into the mixing chamber 31 together with the propellant gas, where the two phases are further mixed to form a liquid-in-gas dispersal. The liquid-in-gas dispersal is ejected out of the mixing chamber 31, through a through-opening 55 in side wall 56 of the nozzle 20, and out of nozzle orifice 21 into the sponge 16. The moveable part 29 can be held in the valve-open position for any desired amount of time, e.g. until the pressure within the container is substantially equal to the pressure outside of the dispenser system.

The liquid inlet 48 can have a cross-sectional opening area of $8 \times 10^{-3}$ to $100 \times 10^{-3}$ mm$^2$ and the constricted section can have a cross-sectional opening area that is at least 150% larger than the cross-sectional opening area of the liquid inlet.

Figure 6:
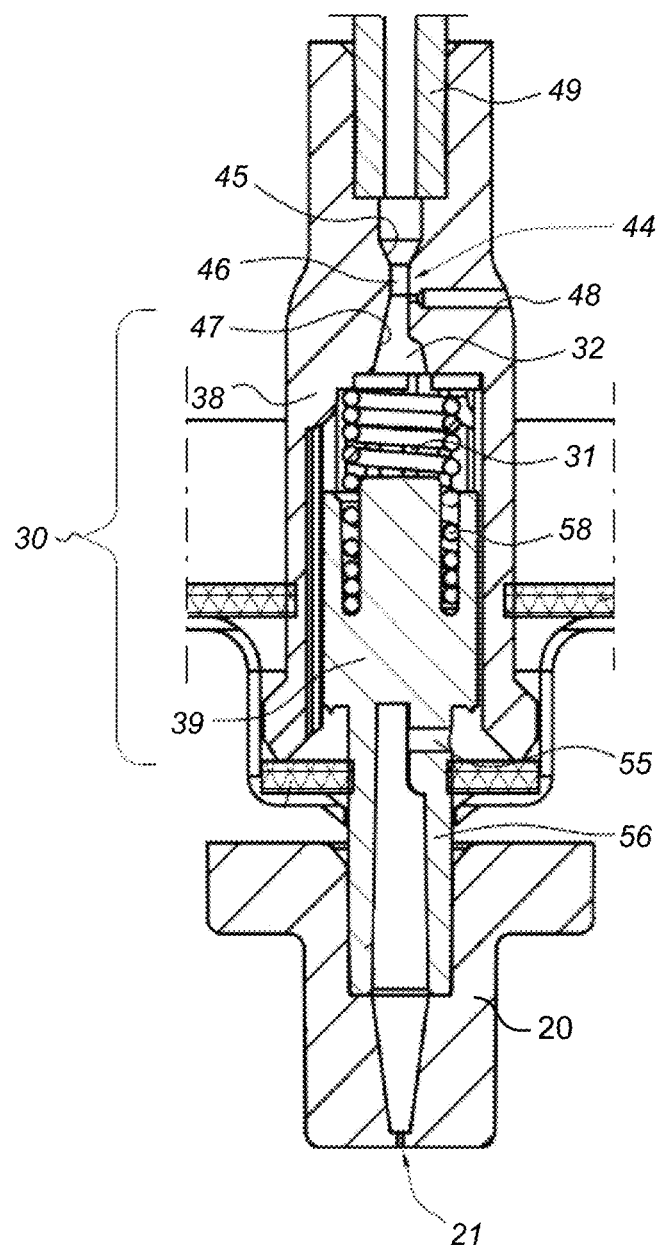
FIG. 6 shows a cross-sectional view of a valve arrangement suitable for use in embodiments of the present invention.

A spring 58 biases the moveable part 39 into the valve-closed position (not shown in FIG. 6). In the valve closed position, the opening 55 is sealed (e.g. with a sealing gasket) and the cryogenic dispersion cannot exit the mixing chamber 31 through the nozzle 20. The valve 30 can be moved to its open position my moving the moving part 39 in a proximal direction with respect to the fixed part 38. Pushing the reservoir 12 (and the fixed part 38) distally with respect to the nozzle 20 thus opens the valve. In this manner, the actuatable valve 30 can be actuated to an open configuration for delivering cryogenic fluid by pushing the device against the skin.

It will be appreciated that the same valve assembly 30 can be combined with alternative actuation mechanisms that allow the moving part 39 to be pushed proximally with respect to the reservoir 12. For example, the lever 18 shown in FIG. 1 can be configured to move the moving part 39 against the bias of the spring 58 to open the valve 30 for dispensing cryogenic fluid.

Further details regarding the Venturi dispense system described above are provided in PCT Application No. PCT/EP2018/069167, the entire contents of which is incorporated herein by reference. The present invention encompasses embodiments in which the Venturi arrangement described in PCT/EP2018/069167 are combined with the spacer and porous material described here. The combination of Venturi dispense system, such as the one describe herein and in PCT/EP2018/069167 may advantageously allow sustained and continuous delivery of cryogenic fluid to the porous material, and thus continuous application of cryogenic fluid to the area to be treated. Continuous application of cryogenic fluid may improve the efficiency of the device since more cooling fluid is applied to the treatment site, and less is lost to the surrounding environment.

It should be noted that the combination of the continuous flow of cryogen provided by the valve assembly described with reference to FIG. 6 may be particularly advantageous in embodiment of the present invention because such a valve assembly can provide for controlled and continuous dispensing of cryogenic fluid to the sponge 16 during treatment, in contrast to pre-loading the sponge with cryogen before treatment. This can allow a longer effective treatment time, which may improve treatment outcomes, especially for larger skin lesions.

So in view of continuous dispensing of cryogenic fluid for longer effective treatment time, the present invention may further relate to a method of applying a cryogenic fluid to the treatment area using the applicator, wherein the method comprises the steps of bringing the porous material 16 into contact with the treatment area; actuating the actuatable valve; and maintaining actuation of the valve for continuously delivering the cryogenic fluid to the treatment area, i.e. through the porous material.

As mentioned hereinabove, the actuation of the valve may be achieved through a lever 18 as depicted in FIG. 1 or through the spacer 14 being moveable with respect to the nozzle 20 and/or the reservoir 12 from the first to the second position.

In an embodiment, actuation of the valve is maintained for at least 10 seconds, e.g. 25 seconds, e.g. 30 seconds, to achieve sufficiently long treatment time. In an embodiment, the treatment area may be a skin area comprising one or more warts, moles, freckles, skin tags, and/or age spots, which can be effectively treated for achieving improved appearance of the skin.

As mentioned above, the cryogenic fluid contained in the reservoir preferably comprises a liquid phase L and a gas phase G, with the liquid phase L in direct contact and in equilibrium with a gas phase G at a pressure of 2.5-8 bar, said liquid phase L comprising at least 50 wt. % liquefied dimethyl ether.

Besides dimethyl ether the liquid phase L may contain other components such as propellants other than dimethyl ether, keratolytics (e.g. glycolic acid or salicylic acid), emollients, antioxidants, trichloroacetic acid, dichloroacetic acid, monochloroacetic acid, and co-solvents.

Anti-inflammatory agents and anaesthetic agents may also be included in any suitable cryogenic fluid mix contained within the reservoir. Additionally, or alternatively, and anti-viral agent may also be included. Suitable anti-inflammatory agents include:

In one embodiment of the invention the liquid phase L contains at least 90 wt. % dimethyl ether. More preferably, the liquid phase L consists of dimethyl ether and is in equilibrium with a gas phase G that also consists of dimethyl ether.

In another embodiment, the liquid phase L contains at least 90 wt. %, more preferably at least 95 wt. % of a mixture of dimethyl ether and one or more alkanes selected from propane, n-butane and isobutane. More preferably, the liquid phase L and the gas phase G consist of a mixture of dimethyl ether and said one or more alkanes.

The liquid phase L preferably contains at least 90 wt. %, more preferably at least 95 wt. % of a mixture of dimethyl ether and propane. More preferably, the liquid phase and the gas phase consist of a mixture of dimethyl ether and propane.

According to a particularly preferred embodiment, the mixture of dimethyl ether and the one or more alkanes contains dimethyl ether and the one or more alkanes in a weight ratio of 1:1 to 9:1, more preferably of 3:2 to 5:1 and most preferably of 2:1 to 4:1.

The present invention has been described above with reference to a number of non-exemplary embodiments. Features of the above-described embodiments can be combined and modifications may be made without departing from the scope of the invention.

The invention claimed is:

1. An applicator for applying cryogenic fluid to a treatment area, the applicator comprising:
a reservoir configured to contain the cryogenic fluid comprising a gas phase and a liquid phase;
a nozzle arranged in fluid communication with the reservoir to allow dispensing of cryogen from the reservoir through an open distal end of the nozzle to a treatment area;
an actuatable valve configured to selectively allow a flow of cryogenic fluid from the reservoir through the open distal end of the nozzle;
an actuator configured to selectively actuate the actuatable valve;
a spacer extending distally beyond the distal end of the nozzle, the spacer comprising a skin contacting surface at its distal end;
a porous material is provided at least between the open end of the nozzle and the skin contacting surface of the spacer, wherein the porous material is configured to be brought into contact with the treatment area, and wherein the actuatable valve comprises
a mixing chamber and comprising an inlet and an outlet, wherein the inlet comprises a Venturi tube having an entry cone for receiving gas phase from the reservoir, an exit cone and a constricted section that connects the entry cone with the exit cone, said constricted section or said exit cone comprising a liquid inlet for receiving liquid phase from the reservoir, the liquid inlet having a first cross-sectional opening area and the constricted section having a second cross-sectional opening area that is at least 150% larger than the first cross-sectional area, and wherein the nozzle is connected to the outlet of the mixing chamber.

2. The applicator according to claim 1, wherein the distal end of the nozzle is spaced from the skin contacting surface of the spacer by a minimum distance D1, wherein D1 is preferably between 2 mm and 15 mm, more preferably between 4 mm and 8 mm.

3. The applicator according to claim 2, wherein the distance between the between the skin contacting surface and the open end of the nozzle is variable between the minimum distance D1 and an initial distance D0, wherein D0 is greater than D1.

4. The applicator according to claim 2, wherein the spacer is moveable with respect to:
the nozzle; and/or
the reservoir;
from a first position to a second position to actuate the actuatable valve, and wherein the distance D1 is defined with the spacer in the second position.

5. The applicator according to claim 1, wherein the spacer comprises one or more of:
a deformable spacer, e.g. a spring;
and/or
a fixed projection.

6. The applicator according to claim 1, wherein the skin contacting surface is configured to define a perimeter around the area to be treated.

7. The applicator according to claim 1, wherein the skin contacting surface defines a plane P, and wherein:
a distal surface of the porous material extends in the plane P; or
a distal end of the porous material projects distally beyond plane P when the applicator is not in use.

8. The applicator according to claim 1, further comprising at least one flange, extending in a transverse direction with respect to the longitudinal axis of the applicator, and wherein the at least one flange preferably comprises a first flange and second flange, said first flange extending in substantially opposing directions.

9. The applicator according to claim 1, wherein the porous material comprises a foam or sponge having an open cell foam in at least a portion thereof.

10. The applicator according to claim 9, wherein the sponge comprises a region of open-cell foam at its distal end, and a region of closed-cell foam at its proximal end.

11. The applicator according to claim 9, wherein the sponge comprises a longitudinal cross-sectional profile selected from the following:
a tapered profile;
a spherical profile; and/or
an elliptical profile.

12. The applicator according to claim 9, wherein the sponge comprises at its distal end a non-planar distal surface comprising a circumferential wall portion, and a recessed central portion, wherein the circumferential wall portion extends at least partially around a perimeter of the recessed portion.

13. The applicator according to claim 1, wherein the porous material and/or the spacer comprise a thermo-chromic composition, e.g. cyanidin chloride with dodecyl gallate and hexadecanoic acid.

14. The applicator according to claim 1, wherein the reservoir contains the cryogenic fluid, the cryogenic fluid optionally comprising a pharmacologically active agent, or a chemically active agent, such as one or more of the following:
an anaesthetic agent;
an antibacterial agent;
an antiviral agent;
an antiinflammatory agent; or
a keratolytic agent.

15. A kit comprising the applicator of claim 1, wherein the porous material is removably mounted on the nozzle, and the kit comprises additional porous components having different shapes.

16. A method of applying a cryogenic fluid to a treatment area, comprising the steps of
  providing an applicator according to claim 1;
  filling the reservoir of the applicator with the cryogenic fluid;
  bringing the porous material of the applicator into contact with the treatment area;
  pressing the spacer against a skin portion oadjacent to the treatment area, thereby actuating the actuatable valve of the applicator such that the cryogenic fluid is delivered from the reservoir through the nozzle of the applicator to the porous material; and
  maintaining actuation of the actuatable valve for at least 10 seconds for continuously delivering the cryogenic fluid to the treatment area.

17. The method of claim 16, wherein the treatment area is a skin treatment area comprising one or more warts, moles, freckles, skin tags, and/or age spots.

\* \* \* \* \*